(12) United States Patent
Kapitan et al.

(10) Patent No.: US 11,420,927 B2
(45) Date of Patent: Aug. 23, 2022

(54) PROCESS FOR THE MANUFACTURE OF ALKYLFLUOROACRYLATE

(71) Applicant: Patheon Austria GmbH & Co KG, Linz (AT)

(72) Inventors: Peter Kapitan, Linz (AT); Alexander Sajtos, Leonding (AT)

(73) Assignee: Patheon Austria GMBH & Co KG, Linz (AT)

( * ) Notice: Subject to any disclaimer, the term of this patent is extended or adjusted under 35 U.S.C. 154(b) by 351 days.

(21) Appl. No.: 14/409,522

(22) PCT Filed: Jun. 25, 2013

(86) PCT No.: PCT/EP2013/063324
§ 371 (c)(1),
(2) Date: Dec. 19, 2014

(87) PCT Pub. No.: WO2014/001365
PCT Pub. Date: Jan. 3, 2014

(65) Prior Publication Data
US 2015/0368178 A1   Dec. 24, 2015

(30) Foreign Application Priority Data

Jun. 25, 2012  (EP) ................... 12173485

(51) Int. Cl.
*C07C 67/54*   (2006.01)
*C07C 67/343*  (2006.01)
*C07C 67/52*   (2006.01)
*C07C 67/32*   (2006.01)

(52) U.S. Cl.
CPC .............. *C07C 67/54* (2013.01); *C07C 67/32* (2013.01); *C07C 67/343* (2013.01); *C07C 67/52* (2013.01)

(58) Field of Classification Search
CPC ....... C07C 69/00; C07C 69/65; C07C 69/653; C08F 20/00
USPC ....................................................... 560/210
See application file for complete search history.

(56) References Cited

U.S. PATENT DOCUMENTS

| 2,454,663 | A   | 11/1948 | McGinty |
| 3,075,002 | A   | 1/1963  | Sedlak |
| 3,262,967 | A   | 7/1966  | Sedlak et al. |
| 3,262,968 | A   | 7/1966  | Sedlak et al. |
| 6,509,134 | B2* | 1/2003  | Ito .................. G03F 7/0046 430/270.1 |
| 9,000,210 | B2  | 4/2015  | Kreis et al. |

FOREIGN PATENT DOCUMENTS

| CN | 102211998   |   | 10/2011 |
| CN | 102211998   | A | 10/2011 |
| CN | 102212000   | A | 10/2011 |
| CN | 102731304   |   | 10/2012 |
| CN | 102731304   | A | 10/2012 |
| CN | 102757347   |   | 10/2012 |
| CN | 102757347   | A | 10/2012 |

OTHER PUBLICATIONS

International Search Report and Written Opinion for PCT/EP2013/063324, dated Sep. 6, 2013, 10 pages.
International Preliminary Report on Patentability for PCT/EP2013/063324, dated Oct. 16, 2014, 7 pages.
The First Office Action for PCT Application in Chinese National Phase Application No. 201380033307.5, dated Nov. 4, 2015, 12 pages.
Chinese Second Office Action dated Jul. 12, 2016, CN Application No. 201380033307.5 (15 pages).
Chinese Rejection Decision dated Jan. 18, 2017, CN Application No. 201380033307.5 (12 pages).
Wuyang Chemical Co., Ltd. (http://www.everychina.com/buy/c-z1408fc4/p-44412143-petroleum_ether_140_150_petroleum_ether.html) (2 pages).
Wuyang Chemical Co., Ltd. (http://www.everychina.com/buy/c-z1408fc4/p-44412148-petroleum_ether_120_130_petroleum_ether.html) (2 pages).
Wuyang Chemical Co., Ltd. (http://www.everychina.com/buy/c-z1408fc4/p-44412146-petroleum_ether_100_120_petroleum_ether.html) (2 pages).
Breckland Scienfific, Safety Data Sheet (http://www.brecklandscientific.co.uk/v/vspfiles/MSDS/S3101257.pdf) (7 pages).
Acros Organics, Geel, Belgium (http://www.acros.com) (2 pages).
Fisher Scientific Company LLC (https://www.fishersci.com/us/en/catalog/search/products?keyword=petroleum+ether&nav) (6 pages).
"Petroleum Ether Aliphatic Hydrocarbon Mixture CAS No." Journal of Chemical Education, vol. 78 No. 12 (2001) p. 1588.
Notice of Reasons for Rejection dated Jan. 4, 2017 from corresponding Japanese Patent Application No. P2015-517811 filed on Dec. 22, 2014 based on PCT/EP2013/063324 filed on Jun. 25, 2013.
Phenix, Alan, "Generic Hydrocarbon Solvents: a Guide to Nomenclature," WAAC Newsletter, vol. 29, No. 2 (2007) pp. 13-22.
Monson, Richard S., "Methods and Techniques," Advanced Organic Synthesis (1971) p. 4 and 22.
Non-Final Office Action in U.S. Appl. No. 16/895,830 dated Feb. 9, 2022, 10 pages.

* cited by examiner

*Primary Examiner* — Leigh C Maier
*Assistant Examiner* — Everett White
(74) *Attorney, Agent, or Firm* — Raymond G. Arner; Pierce Atwood LLP

(57) ABSTRACT

The invention relates to a process for the manufacture of an alkylfluoroacrylate starting from alkylfluoroacetate and an oxalic acid ester, wherein an alkane liquid under the reaction conditions is applied as the solvent in one of the reaction steps.

10 Claims, No Drawings

PROCESS FOR THE MANUFACTURE OF ALKYLFLUOROACRYLATE

RELATED APPLICATIONS

This application is a U.S. National Stage of International Application No. PCT/EP2013/063324, filed on Jun. 25, 2013, which claims priority to European Patent Application No. 12173485.9, filed Jun. 25, 2012, the entire contents of which are incorporated herein by reference.

The invention relates to a process for the manufacture of an alkylfluoroacrylate.

Crossed Claisen condensation of alkyl monofluoroacetates with esters of formic acid or oxalic acid in the presence of strong bases, followed by a reaction with paraformaldehyde represents one of the most widely used methods for the synthesis of a-fluoroacrylates. This method was first disclosed in 1966 in U.S. Pat. Nos. 3,262,967 and 3,262,968, both improvements of the method of U.S. Pat. No. 3,075,002. The reaction is usually carried out using alkali metal hydrides or alkoxides in high boiling solvents such as tetrahydrofuran (THF), diethylether ($Et_2O$), methyl-tert-butylether (MTBE), dimethylsulfoxide (DMSO) or toluene, such as confirmed in 2011/2012 in CN102731304, CN102211998 and CN102757347. The Claisen condensation to Claisen salt from fluoroacetate and oxalate in the presence of sodium alkoxide or sodium hydride is an equilibrium reaction and after the following reaction with paraformaldehyde, the product contained up to 5% of methyl fluoroacetate MFAc, which cannot be completely removed by distillation. Typical yields of methylfluoroacrylate (MFA) reported in literature are in the range of 33-45%. Isolated MFA contains residual methyl fluoroacetate and solvents. Purification of MFA from starting material, residual solvents and side-products is difficult because of very close boiling points and careful column vacuum distillation is required.

It is the object of the present invention to provide an improved process for the manufacture of alkylfluoroacrylate with high purity in high yield and easy isolation.

The invention now relates to a process for the manufacture of an alkylfluoroacrylate, comprising the following steps:
A. an alkylfluoroacetate with an ester of formic acid or oxalic acid is reacted in the presence of a base and a suitable solvent in a crossed Claisen condensation resulting in a Claisen salt,
B. the Claisen salt obtained in step A is optionally filtered off and washed with a suitable solvent,
C. the Claisen salt obtained in step A or B is reacted with paraformaldehyde and
D. the alkylfluoroacrylate obtained in step C is isolated using a suitable solvent, wherein the solvent in at least one of steps A to D comprises an alkane which is liquid under the reaction conditions of steps A, B, C and/or D. Step B in the process of the invention can be performed or can be skipped. Preferably, the solvent in at least step C and optionally in one of steps A, B or D comprises an alkane which is liquid under the reaction conditions of the steps in which the alkane is applied. More preferably, the solvent in steps C and D comprises an alkane which is liquid under the reaction conditions of steps C and D. An alkane being liquid under the reaction conditions means that the alkane particles are free to flow, so while the alkane has a definite volume, it does not have a definite shape.

Surprisingly, the process according to the invention leads to an improved isolated yield of in-spec product. For the purpose of this invention, in-spec product means that impurities are virtually absent, and that for example the methylfluoroacetate level is below 0.5 wt % and the dimethyl carbonate level is below 2.0 wt %. Residual solvents (such as methanol and MTBE) are specified to be maximum 1.0 wt % each. Furthermore, the process according to the invention allows easy solvent recycling. A low boiling alkane instead of MTBE or THF has been found a very convenient solvent for the reaction and isolation of the product. Preferably, the alkane applied in the process according to the invention is a C5-C8 alkane, hence pentane, hexane, heptane or octane. More preferably, the alkane is pentane or hexane. Most preferably, the alkane is pentane. In the light of the invention the term pentane covers all isomers including for example n-pentane, iso-pentane or cyclopentane. For example technical grade pentane applied is defined with a boiling point which reflects the content of the isomers.

The invention also relates to a process for the manufacture of methylfluoroacrylate or ethylfluoroacrylate. More preferably, the invention relates to a process for the manufacture of methylfluoroacrylate.

The ester of formic acid or oxalic acid in the process according to the invention is selected such that it is in line with the alkyl-type of the targeted alkylfluoroacrylate. So when targeting for methylfluoroacrylate, the ester of oxalic acid is dimethyloxalate, when targeting for ethylfluoroacrylate, the selected ester of oxalic acid is diethyloxalate and so forth. In one aspect, the invention relates to the process according to the invention, wherein the ester of oxalic acid is dimethyloxalate or diethyloxalate. More preferably, the ester of oxalic acid is dimethyloxalate.

Then, the invention relates to a process according to the invention wherein the base in the Claisen condensation reaction of step A is a metal alkoxide represented by the formula MOR, wherein M is sodium or potassium and R is a C1-C4 alkyl group, thus methyl, ethyl, propyl or butyl. The invention also relates to a process according to the invention wherein the base in the Claisen condensation reaction is a metal alkoxide of the formula MOR in a C1-C4 alcohol, hence in methanol, ethanol, propanol or butanol. Preferably, the base in the Claisen condensation reaction is sodium methoxide in methanol.

The invention also relates to a process according to the invention, wherein the solvent in the Claisen condensation of step A is an alkane, methyl-tertbutylether or THF. Preferably, the solvent is methyl-tert-butylether or an alkane. More preferably, the solvent is an alkane, even more preferably pentane or hexane, most preferably pentane.

The solvent for the washing of step B can be MTBE or alkane.

As solvent for the isolation of step D an alkane can be used. More preferably, this solvent is pentane or hexane. Even more preferably this solvent is pentane.

The invention also relates to a process according to the invention wherein the isolation of step D comprises a filtration and a distillation.

Furthermore, the invention relates to a process according to the invention wherein alkylfluoroacrylate obtained after the reaction with paraformaldehyde is quenched with water before isolation. The invention also relates to a process wherein the methylfluoroacrylate obtained after the reaction with paraformaldehyde is quenched with water before isolation.

The invention brings the following advantages: methylfluoroacrylate was isolated after distillation with a purity of more than 99.5 wt % and the material obtained meets the specifications, i.e. it is high quality product. Low content of residual methylfluoroacetate and dimethylcarbonate in isolated methylfluoroacrylate are essential for the next steps. Residual methylfluoroacetate is critical because of its very high toxicity and dimethylcarbonate serves as inhibitor for polymerization.

| Parameter | new process (example 2) | old process (example A) |
|---|---|---|
| Purity of MFA | 99.5 wt % | 92.8 wt % |
| Dimethyl carbonate | 0.2 wt % | 3.3 wt % |
| Methyl fluoroacetate | 0.2 wt % | 0.7 wt % |

The methylfluoroacrylate was isolated in 10-20% more yield of inspec product as compared to the processes of the prior art. Since there is no sodium hydride or other harmful base applied in the process, there is a lower risk involved. The reaction is carried out at lower temperatures. Since the Claisen salt is crystallized under new reaction conditions, there is no precipitation on the reactor wall and stirrer. The filtration and washing of the salt is significantly easier. Pentane serves as an anti-solvent in the Claisen condensation and with its lower boiling point is a very convenient solvent for the isolation of MFA. Recovery of pentane is much easier as compared to mixtures of MTBE or THF with methanol. Handling of sodium methoxide in methanol in manufacture is much easier compared to sodium hydride. The reaction in pentane/methanol is carried out 3 times more concentrated. It can significantly reduce the number of batches and costs for the manufacture.

The invention further relates to all possible combinations of different embodiments and/or preferred features according to the process according to the invention as described herein.

The invention will be elucidated with reference to the following examples, without however being restricted by these:

EXAMPLES

Comparative Example A

Original Process

Sodium hydride (NaH) (60% in oil, 20.9 g, 1.2 equiv.) and methyl-tert-butyl-ether (MTBE) (100 mL) were charged to the reactor at room temperature. Catalytic amount of methanol (0.8 mL) was added dropwise and the suspension was heated to 30° C.

Step A

In a separate reactor dimethyl oxalate (51.5 g, 1.1 equiv.) was dissolved in MTBE (350 mL) and methyl fluoroacetate (MFAc) (40.0 g) was added. Resulting solution was added over 10-12 hours to a suspension of sodium hydride in MTBE at 30-35° C. The resulting slurry was stirred for additional 12 h at 30-35° C. then cooled to 5-10° C.

Step C

Paraformaldehyde (15.7 g, 1.2 equiv.) was added in 10 portions and the suspension was stirred at 5-10° C. for additional 5 h. The solid was filtered off and washed with MTBE (150 mL). The filtrate (acrylate) was distilled in vacuum with column (Sulzer, 8 theoretical plates) to remove MTBE and subsequently MFA was distilled at 40° C./100-75 mbar.

There was 58% yield prior to distillation, leading to 35-40% isolated yield after distillation. However, off-spec product was obtained because of residual methyl fluoroacetate and dimethyl carbonate (0.7 wt % methyl fluoroacetate, 3.3 wt % dimethyl carbonate).

Comparative Example B

Isolation of Claisen Salt (Removal of Residual Methyl Fluoroacetate and Dimethyl Carbonate)

Step A

NaH (60% in oil, 20.9 g, 1.2 equiv.) and MTBE (100 mL) were charged to the reactor at room temperature. Catalytic amount of methanol (0.8 mL) was added dropwise and the suspension was heated to 30° C.

In a separate reactor dimethyl oxalate (51.5 g, 1.1 equiv.) was dissolved in MTBE (350 mL) and methyl fluoroacetate was added. Resulting solution was added over 10-12 hours to a suspension of sodium hydride in MTBE at 30-35° C.

Step B

The suspension was cooled to 10° C. and the Claisen salt was filtered off. The filter cake was washed twice with MTBE (2×150 mL).

Step C

The wet salt and MTBE (300 mL) was charged to the reactor and the suspension was cooled to 5-10° C. Paraformaldehyde (15.7 g, 1.2 equiv.) was added in 10 portions and the suspension was stirred at 5-10° C. for additional 5 h.

Step D

The solid was filtered off and washed with MTBE (150 mL). The filtrate (acrylate) was analyzed by GC.

There was 60% yield prior to distillation and after distillation there was 35-40% isolated yield of in-spec product, i.e. there was no unreacted methyl fluoroacetate and dimethyl carbonate.

In addition MTBE as solvent complicate isolation of acrylate, as distillation needs to be carried out at temperature<45° C. for safety reasons (otherwise spontaneous, very exothermic polymerization can take place). Therefore vacuum distillation is required, which worsens separation of acrylate from MTBE (boiling point of MFA is 90.5°-91.75 C at atmospheric pressure).

Comparative Example C

Claisen Condensation with NaOMe in Methanol

Step A

Solid sodium methoxide (14.8 g, 1.2 equiv.) was dissolved in methanol (150 mL) at 0-20° C. and dimethyl oxalate (28.2 g, 1.1 equiv.) was added. The mixture was stirred for 15 min at 20-25° C. followed by addition of methyl fluoroacetate (20.0 g). Resulting solution was heated to 30° C. and stirred at 30° C. for 24 h.

Step C

The reaction mixture was cooled to 10-15° C. and paraformaldehyde was added in several portions. Resulting suspension was warmed to 25° C. and stirred for additional 1 hour.

The suspension was analyzed by GC.

Only 58% conversion of methyl fluoroacetate was reached.

Comparative Example D

Claisen Condensation with NaOMe in MTBE

Step A

Solid sodium methoxide (14.8 g, 1.2 equiv.) was suspended in MTBE (250 mL) at 20-25° C. and dimethyl oxalate (28.2 g, 1.1 equiv.) was added. The suspension was stirred for 15 min at 20-25° C. followed by slow addition of methyl fluoroacetate (20.0 g). Resulting thick slurry was heated to 30° C. and stirred at 30° C. for 24 h.

Step C

The reaction mixture was cooled to 10-15° C. and paraformaldehyde was added in several portions. Resulting suspension was warmed to 25° C. and stirred for additional 1 hour.

The suspension was analyzed by GC.

Only 78% conversion of methylfluoroacetate was reached.

Comparative Example E

Claisen Condensation with 30% NaOMe Solution in MTBE

Step A

Dimethyl oxalate (14.7 g, 1.1 equiv.) was dissolved in MTBE (140 mL) at 20-25° C. followed by addition of methyl fluoroacetate (10.0 g). The mixture was stirred for 15 min at 20-25° C. and 30% NaOMe solution in methanol (24.3 g, 1.25 equiv.) was added dropwise.

Step B

The resulting solution was stirred for 45 h at 20-25° C. (crystallization observed after 2 h at 20-25° C.). The suspension was cooled to 10° C., the Claisen salt was filtered off and washed twice with MTBE (2×40 mL).

Step C

The wet salt and MTBE (70 mL) was charged to the reactor and the suspension was cooled to 5-10° C. Paraformaldehyde (4.0 g, 1.2 equiv.) was added in 10 portions and the suspension was stirred at 5-10° C. for additional 5 h.

Step D

The reaction mixture was quenched with water (63 mL) and the aqueous phase extracted once with MTBE (90 mL).

Combined organic phase was analyzed by quantitative GC. With this reaction 95% conversion of methylfluoroacetate was reached. The yield was 70% of in-spec methyl fluoroacrylate prior to distillation.

Example 1

Isolation of Methyl Fluoroacrylate from Pentane

Step A

NaH (60% in oil, 20.9 g, 1.2 equiv.) and MTBE (100 mL) were charged to the reactor at room temperature. Catalytic amount of methanol (0.8 mL) was added dropwise and the suspension was heated to 30° C.

In a separate reactor dimethyl oxalate (51.5 g, 1.1 equiv.) was dissolved in MTBE (350 mL) and methyl fluoroacetate was added. Resulting solution was added over 10-12 hours to a suspension of sodium hydride in MTBE at 30-35° C.

Step B

The suspension was cooled to 20° C. and the Claisen salt was filtered off. The filter cake was washed twice with MTBE (2×100 mL) and three times with pentane (3×150 mL).

Step C

The wet salt and pentane (300 mL) was charged to the reactor and the suspension was cooled to 5-10° C. Paraformaldehyde (15.7 g, 1.2 equiv.) was added in 10 portions and the suspension was stirred at 5-10° C. for additional 5 h.

Step D

The solid was filtered off and washed with pentane (150 mL). The filtrate (acrylate) was distilled in vacuum with column (Sulzer, 8 theoretical plates) to remove MTBE and subsequently MFA was distilled at 40° C./100-75 mbar.

There was 67% yield prior to distillation and after distillation there was 50% isolated yield of in-spec product, i.e. unreacted methyl fluoroacetate and dimethylcarbonate were not present in isolated product.

Example 2

Claisen Condensation with 30% NaOMe Solution in Pentane

Step A

Dimethyl oxalate (28.2 g, 1.1 equiv.) was suspended in pentane (100 mL) at 20-25° C. followed by addition of methyl fluoroacetate (20.0 g). The mixture was stirred for 15 min at 20-25° C. (two clear phases) and 30% NaOMe solution in methanol (48.9 g, 1.25 equiv.) was added dropwise. The resulting turbid solution was stirred for 24 h at 20-25° C. (crystallization observed after 2 h at 20-25° C.).

Step B

The suspension was cooled to 0° C., the Claisen salt was filtered off and washed with pentane (3×40 mL).

Step C

The wet salt and pentane (120 mL) was charged to the reactor and the suspension was cooled to 5-10° C. Paraformaldehyde (4.0 g, 1.2 equiv.) was added in 10 portions and the suspension was stirred at 5-10° C. for additional 5 h.

Step D

The reaction mixture was quenched with water (115 mL) and the aqueous phase extracted once with pentane (2×60 mL). Combined organic phase was analyzed by quantitative GC.

With this reaction 93% conversion of methyl fluoroacetate was reached. The yield was 66% prior to distillation. Methyl fluoroacrylate was isolated in a yield of 58% after distillation.

Example 3

Claisen Condensation with Less 30% NaOMe Solution in Less Pentane as Compared to Example 2

Step A

Dimethyl oxalate (28.2 g, 1.1 equiv.) was suspended in pentane (40 mL) at 20-25° C. followed by addition of methyl fluoroacetate (20.0 g). The mixture was stirred for 15 min at 20-25° C. (two clear phases) and 30% NaOMe solution in methanol (41.0 g, 1.05 equiv.) was added dropwise. The resulting turbid solution was stirred for 24 h at 20-25° C. (crystallization observed after 2 h at 20-25° C.).

Step B

The suspension was cooled to 0° C., the Claisen salt was filtered off and washed with pentane (3×40 mL).

Step C

The wet salt and pentane (120 mL) was charged to the reactor and the suspension was cooled to 5-10° C. Paraformaldehyde (4.0 g, 1.2 equiv.) was added in 10 portions and the suspension was stirred at 5-10° C. for additional 5 h.

Step D

The reaction mixture was quenched with water (115 mL) and the aqueous phase extracted once with pentane (2×60 mL). Combined organic phase was analyzed by quantitative GC.

With this reaction 90% conversion of methyl fluoroacetate was reached. The yield was 65% prior to distillation. Methyl fluoroacrylate was isolated in a yield of 55% after distillation.

Hypothetical Example 4

Claisen Condensation with 30% NaOMe Solution in Hexane

Step A

Dimethyl oxalate (28.2 g, 1.1 equiv.) is suspended in hexane (40 mL) at 20-25° C. followed by addition of methyl fluoroacetate (20.0 g). The mixture is stirred for 15 min at 20-25° C. (two clear phases) and 30% NaOMe solution in methanol (48.9 g, 1.25 equiv.) is added dropwise. The resulting turbid solution is stirred for 24 h at 20-25° C.

Step B

The suspension is cooled to 0° C., the Claisen salt is filtered off and washed with hexane (3×40 mL).

Step C

The wet salt and hexane (120 mL) are charged to the reactor and the suspension is cooled to 5-10° C. Paraformaldehyde (4.0 g, 1.2 equiv.) is added in 10 portions and the suspension is stirred at 5-10° C. for additional 5 h.

Step D

The reaction mixture is quenched with water (115 mL) and the aqueous phase extracted once with hexane (2×60 mL). Organic phases are combined and the product is purified by vacuum distillation.

The yield reached prior to distillation is expected to be in line with the yields obtained for the pentane examples.

Hypothetical Example 5

Claisen Condensation of Ethyl Fluoroacetate with 30% NaOMe Solution in Pentane

Step A

Diethyl oxalate (34.9 g, 1.1 equiv.) is suspended in pentane (40 mL) at 20-25° C. followed by addition of ethyl fluoroacetate (23.0 g). The mixture is stirred for 15 min at 20-25° C. and 30% NaOMe solution in methanol (48.9 g, 1.25 equiv.) is added dropwise. The resulting solution is stirred for 24 h at 20-25° C.

Step B

The suspension is cooled to 0° C., the Claisen salt is filtered off and washed with pentane (3×40 mL).

Step C

The wet salt and pentane (120 mL) are charged to the reactor and the suspension is cooled to 5-10° C. Paraformaldehyde (4.0 g, 1.2 equiv.) is added in 10 portions and the suspension is stirred at 5-10° C. for additional 5 h.

Step D

The reaction mixture is quenched with water (115 mL) and the aqueous phase extracted once with pentane (2×60 mL). Organic phases are combined and the product is purified by vacuum distillation.

The yield reached prior to distillation is expected to be in line with the yield obtained for the methylfluoroacrylate examples.

The invention claimed is:
1. A process for the manufacture of a methylfluoroacrylate, comprising the following steps:
A. a methylfluoroacetate with an ester of oxalic acid is reacted in the presence of a base and a suitable solvent in a crossed Claisen condensation reaction resulting in a Claisen salt;
B. the Claisen salt obtained in step A is optionally filtered off and washed with a suitable solvent;
C. the Claisen salt obtained in step A or B is reacted with paraformaldehyde in a suitable solvent;

D. the methylfluoroacrylate obtained in step C is isolated using a suitable solvent, wherein the methylfluoroacrylate isolated after distillation has a purity of at least 99.5 wt %, contains below 0.5 wt % methylfluoroacetate and below 2.0 wt % dimethyl carbonate;

wherein the solvent in at least steps C and D and optionally in one of steps A or B is an alkane selected from a group consisting of pentane and hexane.

2. The process according to claim 1, wherein the alkane is pentane.

3. The process according to claim 1 or 2, wherein the solvent in steps C and D comprises the alkane.

4. The process according to claim 1, wherein the ester of oxalic acid is dimethyloxalate.

5. The process according to claim 1, wherein the base in the Claisen condensation reaction is a metal alkoxide represented by the formula MOR, wherein M is sodium or potassium and R is a $C_1$-$C_4$ alkyl group.

6. The process according to claim 1, wherein the base in the Claisen condensation reaction is a metal alkoxide of the formula MOR in a $C_1$-$C_4$ alcohol.

7. The process according to claim 1, wherein the base is sodium methoxide in methanol.

8. The process according to claim 1, wherein the solvent in step A is methyl-tert-butylether or pentane.

9. The process according to claim 1, wherein methylfluoroacrylate obtained after the reaction with paraformaldehyde is quenched with water before isolation.

10. The process according to claim 1, wherein the isolation comprises a filtration and a distillation.

* * * * *